United States Patent [19]

Kysela et al.

[11] Patent Number: 4,588,844
[45] Date of Patent: May 13, 1986

[54] PROCESS FOR PREPARING AROMATIC ALDEHYDES

[75] Inventors: Ernst Kysela, Bergisch-Gladbach; Erich Klauke, Odenthal, both of Fed. Rep. of Germany

[73] Assignee: Bayer Aktiengesellschaft, Leverkusen, Fed. Rep. of Germany

[21] Appl. No.: 575,962

[22] Filed: Feb. 1, 1984

[30] Foreign Application Priority Data

Feb. 8, 1983 [DE] Fed. Rep. of Germany ....... 3304202

[51] Int. Cl.$^4$ ................... C07C 47/565; C07C 45/42
[52] U.S. Cl. ...................................... 568/41; 568/436
[58] Field of Search .................... 568/41, 436, 442

[56] References Cited

U.S. PATENT DOCUMENTS

| 3,833,660 | 9/1974 | Smith | 568/436 |
|---|---|---|---|
| 3,974,223 | 8/1976 | Cahoy | 568/436 |
| 4,079,182 | 3/1978 | Savins et al. | 568/436 |
| 4,085,147 | 4/1978 | Rosinger et al. | 568/436 |
| 4,108,904 | 8/1978 | Brown et al. | 568/436 |
| 4,321,412 | 3/1982 | Schoch et al. | 568/436 |

FOREIGN PATENT DOCUMENTS

| 0035624 | 9/1981 | European Pat. Off. |
| 2261754 | 9/1975 | France |
| 2086882 | 5/1982 | United Kingdom |
| 2087378 | 5/1982 | United Kingdom |

OTHER PUBLICATIONS

Noyes et al., *Chemical Reviews,* vol. 38, pp. 227, 230, (1946).
Diehl et al., *Chemical Abstracts,* vol. 42, No. 1241g–1242f, (1948).
Roberts et al., *Basic Principles of Organic Chemistry,* pp. 938–939, N.Y., (1965).
Adams et al., *Organic Reactions,* vol. VIII, pp. 203–205, Wiley, N.Y. (1954).
Liggett et al., *Chemical Abstracts,* vol. 41, No. 110e, (1947).
Kulka, *Chemical Abstracts,* vol. 51, No. 15449d, (1957).
Cardani et al., *Chemical Abstracts,* vol. 53, No. 19937c, (1959).
Ogata et al., *Chemical Abstracts,* vol. 69, No. 51375h, (1968).
Chatterjee et al., *Chemical Abstracts,* vol. 82, No. 97912c, (1975).
Nazaretyan et al., *Chemical Abstracts,* vol. 81, No. 91169y, (1974).
Papenfuhs, et al., *Chemical Abstracts,* vol. 86, No. 173080e, (1977).
Merck, *Chemical Abstracts,* vol. 84, No. 164424b, (1976).

*Primary Examiner*—Natalie Trousof
*Assistant Examiner*—Bruce D. Gray
*Attorney, Agent, or Firm*—Sprung Horn Kramer & Woods

[57] ABSTRACT

Aromatic aldehydes are prepared by formylating the corresponding aromatic compounds with urotropine in the presence of hydrogen fluoride. By the described process certain new aromatic aldehydes can be prepared.

14 Claims, No Drawings

PROCESS FOR PREPARING AROMATIC ALDEHYDES

The invention relates to a process for preparing aromatic aldehydes by formylating the corresponding aromatic compounds with urotropine in the presence of hydrogen fluoride. This invention also relates to new aromatic aldehydes.

It is known to formylate with urotropine phenols or alkyl analines in the presence of glycerol/boric acid or acetic acid (Houben-Weyl VII/1, 199 (1954), Tetrahedron 24, 5001–5010 (1968)). Alkylphenols and alkylbenzenes can be formylated with urotropine in the presence of trifluoroacetic acid (J.O.C. 37 (24) 3973 (1972)). Chlorophenols, nitrophenols and halogenobenzenes can be formylated with urotropine in the presence of polyphosphoric acid (J.C.S. [London], 10741 (1963)).

The known methods are generally only suitable for formylating electron-rich aromatics. The yields of halogenobenzyladehydes are unsatisfactory.

A process has been found for formylating aromatic compounds with urotropine, which is characterised in that the formylation is carried out in the presence of hydrogen fluoride, if desired at elevated temperatures and under elevated pressure.

The process according to the invention is particularly suitable for formylating relatively electrondeficient aromatic compounds.

Aromatic compounds suitable for the process according to the invention are essentially all aromatics, preferably aromatics of the benzene series, which do not change under the reaction conditions and have a reactivity which is about that of chlorobenzene.

Preferred aromatic compounds for the process according to the invention are compounds of the formula

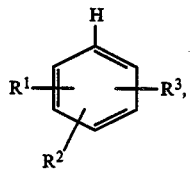

(I)

in which $R^1$, $R^2$ and $R^3$ are identical or different and denote hydrogen, halogen, hydroxyl or optionally fluorine-substituted lower alkyl, lower alkoxy or lower alkylthio.

For the purposes of the invention halogen denotes hereinafter fluorine, chlorine, bromine and iodine, preferably fluorine, chlorine and bromine.

Lower alkyl and the alkyl moiety in lower alkoxy and in lower alkylthio can be herein a straight-chain or branched hydrocarbon radical having 1 to about 8 carbon atoms, preferably 1 to 4 carbon atoms.

The following lower alkyl radicals may be mentioned as examples: methyl, ethyl, propyl, isopropyl, butyl, isobutyl, pentyl, isopentyl, hexyl, isohexyl, heptyl, isoheptyl, octyl and isooctyl.

The following lower alkoxy radicals may be mentioned as examples: methoxy, ethoxy, propoxy, isopropoxy, butoxy, isobutoxy, pentoxy, isopentoxy, hexoxy, isoheptoxy, heptoxy, isoheptoxy, octoxy and isooctyl.

The following lower alkylthio radicals may be mentioned as examples: methylthio, ethylthio, propylthio, isopropylthio, butylthio, isobutylthio, pentylthio, isopentylthio, hexylthio, isohexylthio, heptylthio, isoheptylthio, octylthio and isooctylthio.

The said radicals can be partially or completely substituted by fluorine. In the case of partial substitution, the radicals can contain up to n-1 fluorine atoms (where n denotes the number of hydrogen atoms in the corresponding alkyl radical) in all statistically feasible positions.

The following fluorinated lower alkyl compounds may be mentioned as examples: trifluoromethyl, perfluoroethyl, perfluoroisopropyl, 1,1,2,2-tetrafluoroethyl, hexafluoroisopropyl and 1,1,1-trifluoropropyl.

The following fluorinated lower alkoxy compounds may be mentioned as examples: trifluoromethoxy, perfluoroethoxy, perfluoroisopropoxy, 1,1,2,2-tetrafluoroethoxy, hexafluoroisopropoxy, 3,3,3-trifluoro-n-propoxy and 1,1,1-trifluoro-5-methyl-methoxy.

The following fluoroalkylthio compounds may be mentioned as examples: trifluoromethylthio, perfluoroethylthio, perfluoroisopropylthio, 1,1,2,2-tetrafluoroethylthio, hexafluoroisopropoxy, 3,3,3-trifluoro-n-propylthio and 1,1,1-trifluoro-5-methylhexylthio.

Particularly preferred aromatic compounds for the process according to the invention are compounds of the formula

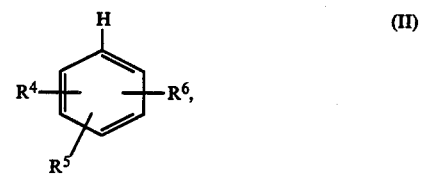

(II)

in which
$R^4$ denotes hydroxyl, alkyl having 1 to 4 carbon atoms, alkoxy having 1 to 4 carbon atoms or alkylthio having 1 to 4 carbon atoms, $R^5$ denotes fluorine, chlorine, bromine, fluoroalkyl having 1 to 4 carbon atoms, fluoroalkoxy having 1 to 4 carbon atoms or fluoroalkylthio having 1 to 4 carbon atoms and $R^6$ denotes hydrogen, hydroxyl, optionally fluorine-substituted alkyl having 1 to 4 carbon atoms, alkoxy having 1 to 4 carbon atoms or alkylthio having 1 to 4 carbon atoms, fluorine, chlorine or bromine, where if $R^6$ denotes fluoroalkyl, fluoroalkoxy or fluoroalkylthio, $R^4$ and $R^5$ can also be hydrogen.

Those aromatic compounds which are substituted by fluorine-containing radicals are particularly preferred for the process according to the invention.

The aromatic compounds for the process according to the invention are known in themselves.

The hydrofluoric acid used for the process according to the invention is generally anhydrous hydrofluoric acid.

0.5 to 5 mol, preferably 1 to 2 mol, of urotropine are generally used in the process according to the invention per mol of aromatic compound.

10 to 100 mol, preferably 25 to 50 mol, of hydrofluoric acid are generally used in the process according to the invention per mol of aromatic compound.

The process according to the invention is generally carried out within the pressure range from atmospheric pressure to 25 bar, preferably from 2 to 15 bar. The pressures according to the invention are established, for example, by the autogenous pressure which results when the process is carried out in an autoclave within the temperature range according to the invention, generally 0° to 180° C.

The process according to the invention can be carried out, for example, as follows:

An autoclave is charged with the aromatic compound, the urotropine and the hydrofluoric acid. The reaction mixture is heated to the reaction temperature and the corresponding reaction pressure becomes established.

When the reaction has ended, the autoclave is let down from the residual pressure, and the reaction mixture is worked up in water.

The process according to the invention can prepare aromatic aldehydes of the formula

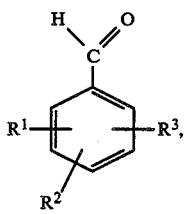

in which
R¹ to R³ have the abovementioned meaning.

The process according to the invention can prepare new aromatic aldehydes of the formula

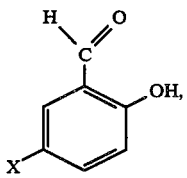

in which X denotes trifluoromethylthio or trifluoromethoxy.

The aromatic aldehydes prepared by the process according to the invention, in particular the new aromatic aldehydes of the formula (IV), are intermediates for preparing plant protection agents preferably insecticides. For example, an oxime can be prepared by reaction with a hydroxylamine in a first stage and then, in a second stage, a phosphone radical can be introduced via an ether bond.

EXAMPLE 1

4-Trifluoromethoxybenzaldehyde (A) with (2-trifluoromethoxybenzaldehyde (B))

0.5 liter (25 Mol) of HF is added with brine cooling (5° C.) to 162 g (1 mol) of trifluoromethoxybenzene and 140 g (1 mol) of urotropine in a V4A stainless steel stirred autoclave. The apparatus is sealed pressuretight and heated to 80° C. for 5 hours. A pressure of 6 to 7 bar becomes established. When the reaction has ended, the crude reaction mixture, which is cooled down to 25° C., is stirred into 1 liter of water and stirred therein at 5° C. for 15 minutes, the organic content is then isolated, and the aqueous phase is extracted with methylene chloride. Crude distillation of the washed organic phases gives 135 g of product (boiling point: 72°-74° C./8 mbar). The products consists of 93% of 4-trifluoromethoxybenzaldehyde (boiling point: 78°-80° C./20mbar) and 6% of 2-trifluoromethoxybenzaldehyde (boiling point: 60°-61° C./20 mbar). The two constituents can be separated by fractional distillation.

EXAMPLE 2

4-Trifluoromethoxybenzaldehyde with (2-trifluoromethoxybenzaldehyde)

162 g (1 mol) of trifluoromethoxybenzene were reacted at 100° C. analogously to Example 1. The crude distillation produced 119 g of product (boiling point: 72°-74° C./18 mbar) consisting to 90% of 4-trifluoromethoxybenzaldehyde and to 8% of 2-trifluoromethoxybenzaldehyde.

EXAMPLE 3

162 g (1 mol) of trifluoromethoxybenzene were employed at 60° C. in the presence of 1 liter (50 Mol) of HF analogously to Example 1. The crude distillation produced 115 g of product (boiling point: 72°-74° C./18 mbar).

EXAMPLE 4

162 g (1 mol) of trifluoromethoxybenzene were reacted at 100° C. in the presence of 0.5 mol of urotropine analogously to Example 1. The crude distillation produced 82 g of product (boiling point: 72°-74° C./18 mbar).

EXAMPLE 5

2-Methyl-5-fluorobenzaldehyde (2-fluoro-5-methyl-benzaldehyde)

110 g (1 mol) of 4-fluorotoluene were reacted analogously to Example 1. The crude distillation produced 80 g of product (boiling point: 83°-85° C./20 mbar) consisting to 80% of 2-methyl-5-fluorobenzaldehyde (boiling point: 82° C./20 mbar) and to 20% of 2-fluoro-5-methylbenzaldehyde.

EXAMPLE 6

4-Fluorobenzaldehyde (2-fluorobenzaldehyde)

96 g of fluorobenzene (1 mol) were reacted at 100° C. analogously to Example 1. The crude distillation produced 37 g of product (boiling point: 65°-68° C./14 mbar) consisting to 87% of 4-fluorobenzaldehyde (boiling point: 64°-65° C./14 mbar) and to 12% of 2-fluorobenzaldehyde (boiling point: 59°-60° C./14 mbar), which can be separated by distillation.

EXAMPLE 7

4-Methyl-5-trifluoromethylbenzaldehyde 160 g of 2-methyltrifluoromethylbenzene (1 mol) were reacted at 100° C. analogously to Example 1. The distillation produced 50 g of 4-methyl-5-trifluoromethylbenzaldehyde (boiling point: 86°-87° C./20 mbar).

EXAMPLE 8

2-Hydroxy-5-trifluoromethoxybenzaldehyde 178 g (1 mol) of 4-trifluoromethoxyphenol were reacted at 100° C. analogously to Example 1. The distillation produced 84 g of 2-hydroxy-5-trifluoromethoxybenzaldehyde (boiling point: 83°-84° C./20 mbar).

EXAMPLE 9

4-Trifluoromethylthiobenzaldehyde 178 g (1 mol) of trifluoromethylthiobenzene were reacted analogously to Example 1. The distillation produced 57 g of 4-trifluoromethylthiobenzaldehyde (boiling point: 88°–89° C./18 mbar).

EXAMPLE 10

2-Hydroxy-5-trifluoromethylthiobenzaldehyde 194 g (1 mol) of 4-trifluoromethylthiophenol were reacted analogously to Example 1. The distillation produced 44 g of 2-hydroxy-5-trifluoromethylthiobenzaldehyde (boiling point: 105°–107° C./20 mbar; melting point: 50°–52° C.).

EXAMPLE 11

4-Chlorobenzaldehyde (2-chlorobenzaldehyde)

112 g (1 mol) of chlorobenzene were reacted at 80° C. analogousLy to ExampLe 1. The Crude distillation produced 106 g of product (boiling point: 90°–92° C./20 mbar) consisting of 75% of 4-chlorobenzaldehyde and of 25% of chlorobenzaldehyde.

What is claimed is:

1. In the process for formylating an aromatic compound to prepare the corresponding aromatic aldehyde which process comprises contacting said aromatic compound with urotropine in the presence of an acid reaction partner at an elevated temperature and under elevated pressure and to hydrolyze the reaction product formed, wherein the improvement comprises
    (a) said aromatic compound being selected from the group consisting of trifluoromethoxybenzene, 4-fluorotoluene, fluorobenzene, 2-methyltrifluoromethylbenzsene, 4-trifluoromethoxyphenol, trifluoromethylthiobenzene, 4-trifluoromethylthiophenol and chlorobenzene; and
    (b) said acid reaction partner being hydrogen fluoride, said hydrogen fluoride being in an amount of 10 to 100 mol of hydrogen fluoride per mol of said aromatic compound,
and subsequently working up the reaction mixture in water.

2. A process according to claim 1, wherein the process is carried out under a pressure ranging from atmospheric pressure to 25 bar.

3. A process according to claim 1, wherein the process is carried out at a temnerature in the range from 0° to 180° C.

4. A process according to claim 1, wherein the process is carried out employing 0.5 to 5 mols of urotropine per mol of aromatic compound.

5. A process according to claim 3, wherein the process is carried out employing 1 to 2 mols of urotropine per mol of aromatic compound.

6. A process according to claim 1, wherein the aromatic compound is trifluoromethoxybenzene.

7. A process according to claim 1, wherein the aromatic compound is 4-fluorotoluene.

8. A process according to claim 1, wherein the aromatic compound is fluorobenzene.

9. A process according to claim 1, wherein the aromatic compound is 2-methyltrifluoromethylbenzene.

10. A process according to claim 1, wherein the aromatic compound is 4-trifluoromethoxyphenol.

11. A process according to claim 1, wherein the aromatic compound is trifluoromethylthiobenzene.

12. A process according to claim 1, wherein the aromatic compound is 4-trifluoromethylthiophenol.

13. A process according to claim 1, wherein the aromatic compound is chlorobenzene.

14. An aromatic aldehyde of the formula

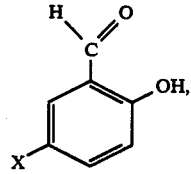

wherein x denotes trifluoromethylthio.

* * * * *